US009617509B2

(12) United States Patent
Li et al.

(10) Patent No.: US 9,617,509 B2
(45) Date of Patent: Apr. 11, 2017

(54) FERMENTATION OF GASEOUS SUBSTRATES

(71) Applicant: LanzaTech New Zealand Limited, Auckland (NZ)

(72) Inventors: Xueliang Li, Skokie, IL (US); Benjamin James Cossey, Auckland (NZ); Simon Richard Trevethick, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 39 days.

(21) Appl. No.: 14/341,731

(22) Filed: Jul. 25, 2014

(65) Prior Publication Data

US 2015/0031099 A1    Jan. 29, 2015

Related U.S. Application Data

(60) Provisional application No. 61/859,768, filed on Jul. 29, 2013.

(51) Int. Cl.
| | |
|---|---|
| C12P 7/14 | (2006.01) |
| C12M 1/34 | (2006.01) |
| C12P 7/06 | (2006.01) |
| C12P 7/54 | (2006.01) |
| C12P 7/18 | (2006.01) |
| C12M 1/21 | (2006.01) |
| C12M 1/00 | (2006.01) |

(52) U.S. Cl.
CPC ............ *C12M 41/40* (2013.01); *C12M 29/02* (2013.01); *C12M 29/08* (2013.01); *C12M 29/18* (2013.01); *C12M 41/02* (2013.01); *C12P 7/065* (2013.01); *C12P 7/18* (2013.01); *C12P 7/54* (2013.01); *Y02E 50/17* (2013.01)

(58) Field of Classification Search
CPC ...... C12M 29/02; C12M 29/08; C12M 41/02; C12M 29/18; C12M 41/40; C12P 7/065; C12P 7/54; C12P 7/18; Y02E 50/17
See application file for complete search history.

(56) References Cited

U.S. PATENT DOCUMENTS

| | | | |
|---|---|---|---|
| 4,952,509 A * | 8/1990 | Wegner | B01D 19/0047 435/301.1 |
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,492,135 B1 | 12/2002 | Larsen | |
| 8,143,037 B2 | 3/2012 | Zahn et al. | |
| 8,178,330 B2 * | 5/2012 | Trevethick | C12M 21/12 435/161 |
| 2011/0244538 A1 * | 10/2011 | Trevethick | C12M 21/12 435/161 |

FOREIGN PATENT DOCUMENTS

| | | |
|---|---|---|
| EP | 117309 | 9/1984 |
| WO | WO98/00558 | 1/1998 |
| WO | WO00/68407 | 11/2000 |
| WO | WO02/08438 | 1/2002 |
| WO | WO2007/117157 | 10/2007 |
| WO | WO2008/028055 | 3/2008 |
| WO | WO2008/115080 | 9/2008 |
| WO | WO2009/064200 | 5/2009 |

OTHER PUBLICATIONS

Fadavi A. et al. "Gas-liquid mass transfer in a novel forced circulation loop reactor", Chemical Engineering Journal, 2005, vol. 112, pp. 73-80.*
Abrini, J. Naveau, H. & Nyns, E. J., Archives of Microbiology, (1994), 161, 345-351.
Vega, J. L. et al., Design of Bioreactors for Coal Synthesis Gas Fermentations, Resources, Conservation and Recycling, (1990), 3. 149-160.
Hensirisak et al., Scale-up of microbubble dispersion generator for aerobic fermentation, Applied Biochemistry and Biotechnology, Oct. 2002, vol. 101, No. 3.
Vega, J. L. et al., Study of Gaseous Substrate Fermentation: Carbon Monoxide Conversion to Acetate. 2. Continuous Culture. Biotech. Bioeng., (1989), 34. 6. 785-793.
Vega, J. L., et al., Study of gaseous substrate fermentations: Carbon monoxide conversion to acetate. 1. Batch culture, Biotechnology and Bioengineering, (1989), 34. 6. 774-784.
Klasson, K. T. et al., Bioreactor design for synthesis gas fermentations, Fuel, (1991), 70, 605-614.
Klasson K. T. et al., Bioreactors for synthesis gas fermentations resources, Conservation and Recycling, (1991), 5, 145-165.
Klasson K. T. et al., Bioconversion of synthesis gas into liquid or gaseous fuels, Enzyme and Microbial Technology, (1992), 14, 602-608.
Liou et al., International Journal of Systematic and Evolutionary Microbiology, (2005), 33, pp. 2085-2091.
Sakai et al., Biotechnology Letters, (2004), 29, pp. 1607-1612.
Svetlichny, V.A. Sokolova T.G. et al., Systematic and Applied Microbiology, (1991), 14, 254-260.

(Continued)

*Primary Examiner* — Satyendra K Singh
(74) *Attorney, Agent, or Firm* — Frank S Molinaro

(57) ABSTRACT

A reactor system is provided for improved fermentation of a gaseous substrate through the introduction of a secondary loop to a forced-circulation loop reactor. The reactor comprises a primary loop through which fermentation broth comprising a gaseous substrate is circulated through a riser segment and a downcomer section by a loop pump. Downstream of the loop pump a portion of fermentation broth is withdrawn from the downcomer section and is directed to the top of the reactor via a secondary loop. Further provided is a method for improving the mass transfer of a gaseous substrate to a fermentation broth in a fermentation vessel comprising a secondary loop. Further provided is a method for reducing foam in the headspace of a fermentation vessel comprising a secondary loop.

15 Claims, 6 Drawing Sheets

(56) References Cited

OTHER PUBLICATIONS

Chang, L.S. et al., Effect of CO partial pressure on cell-recycled continuous CO fermentation by Eubacterium limosum KIST612, (2001), Process Biochemistry, vol. 37, No. 4, pp. 411-421.
Biebl, H., Fermentation of glycerol by Clostridium pasteurianum—batch and continuous culture studies, Journal of Industrial Microbiology & Biotechnology (Jul. 2001) vol. 27, Issue 1, pp. 18-26.
PCT Search Report (PCT/NZ2014/000154) dated Dec. 29, 2014.

* cited by examiner

FERMENTATION OF GASEOUS SUBSTRATES

CROSS REFERENCE TO A RELATED APPLICATION

This application claims priority from Provisional Application No. 61/859,768 filed Jul. 29, 2013, the contents of which are hereby incorporated by reference.

FIELD OF THE INVENTION

This invention relates to systems and methods for improving a forced-circulation external-loop reactor. In particular, the invention introduces a secondary loop to a forced-circulation external-loop reactor that regulates the gas holdup in the reactor and enables improved foam control.

BACKGROUND OF THE INVENTION

Fuels and chemicals produced from synthesis gas (syngas) or CO-containing industrial off-gas represent a prime alternative to fossil fuel and chemicals derived thereof. Chemical catalytic conversion of these gases into fuels or chemicals is expensive or commercially unattractive. Instead, biological conversion of these gases into fuels and chemicals (known as gas fermentation), have several advantages over catalytic processes, including higher specificity, higher yields, lower energy costs and greater resistance to poisoning.

The efficiency of gas fermentation is known to be limited primarily by a low gas-liquid mass transfer rate due to the poor solubility of gaseous substrates (for example, CO and $H_2$) in liquids. The mass transfer efficiency, or volumetric mass transfer rate, is provided as follows:

$$-\frac{dN}{V_R \cdot dt} = k_L a(C^* - C_L)$$

Where $$-\frac{dN}{dt}$$

is the rate at which the gaseous substrate is transferred to the liquid phase; $K_L a$ is the volumetric mass transfer coefficient, consists of the liquid side mass transfer coefficient $k_L$ and the specific mass transfer surface area, a. $C^*$ is the saturation concentration of the gas in the liquid (i.e., the solubility) which is proportional to the partial pressure of the gaseous substrate and $C_L$ is the actual gas concentration in the liquid, the difference between the two, i.e., $(C^*-C_L)$ is the mass transfer driving force. Under pure mass-transfer limited conditions, $C_L \approx 0$. $V_R$ is the wetted volume of the reactor and it is the sum of gas volume and liquid volume.

Thus, in order to improve mass transfer efficiency, one needs to either increase $k_L a$ or the driving force. The driving force can be enhanced by using higher pressure; however, such methods are of high cost as the compression of gas is required. It is generally more preferable to increase $k_L$ and/or a. While $k_L$ is an intrinsic property of the liquid and gas, meaning it is difficult to change, a has a simple relationship with the gas holdup, $\epsilon_G$, and the average bubble radius, $r_b$, both of which can be easily manipulated. The relationship is as follows:

$$a = \frac{3\varepsilon_G}{r_b}$$

The above equation dictates that the specific mass transfer area can be increased by an increase in gas holdup, $\epsilon_G$, or a decrease in bubble size, $r_b$, or a combination of both. Unfortunately, most of such methods tend to generate a large quantity of foam, which may block the pipelines downstream of the bioreactor. Thus, when measures are taken to increase the mass transfer surface area, special attention must to be paid to foam control.

A high mass transfer rate is generally desirable for gas fermentation. However, the process can suffer from substrate inhibition if the mass transfer rate is higher than the maximum reaction rate the microbes can provide. For example, a high dissolved CO concentration results in slow growth of microbes and slow uptake of $H_2$, and if such conditions last for a prolonged period of time, the culture may slowly die out (Design of Bioreactors for Coal Synthesis Gas Fermentations, J. L. Vega, E. C., Clausen and J. L. Gaddy, 1990, Resources, Conservation and Recycling, Vol 3, Pages 149-160; Effect of CO partial pressure on cell-recycled continuous CO fermentation by *Eubacterium limosum* KIST612, I. S. Chang, B. H. Kim, R. W. Lovitt, J. S. Bang, 2001, Process Biochemistry, Vol 37, Page 411-421). Such "oversupply" conditions may occur globally in a small scale, well-mixed reactor, but may also occur locally in a large scale reactor where there is high local dissolved CO concentration, typically at the bottom where the gas is introduced and the CO partial pressure is high.

Therefore, a commercial scaled reactor for gas fermentation needs to provide a high gas-to-liquid mass transfer rate, and also needs to be flexible in order that the mass transfer rate can be regulated when necessary. Effective foam control is also a requirement.

At bench-top scale, gas fermentation is typically carried out in continuous stirred tank reactors (CSTR). However, these are inappropriate for commercial scale application due to high energy consumption and other concerns. Instead, bubble columns with or without internal or external loops may be used for large scale gas fermentation. Forced-circulation external-loop reactors are a type of bubble column reactor where the liquid is forced to circulate between a main column (the riser) and an external loop (the downcomer) by a pump, herein referred to as a loop pump.

In known forced-circulation loop-reactor configurations, the speed of the loop pump has two major effects on the hydrodynamics and mass transfer of the system: (a) an increase in loop pump speed enhances the gas entrainment from the riser to the downcomer, which tends to increase the riser and downcomer holdup, and thus improves mass transfer; (b) an increase in loop pump speed increases the liquid velocity in the riser, which tends to wash out the gas bubbles in the riser quickly and decreases the gas holdup and reduces the gas residence time. Conversely, if the loop pump speed is reduced, the gas bubbles in the riser can stay for a longer period of time, but the gas entrainment into the downcomer will be substantially less, which could reduce the reaction rate in the downcomer and the overall performance of the reactor. In addition, as the gas introduced at the bottom of the riser has high CO content, a low loop pump speed in a deep reactor aggravates substrate inhibition.

Thus, a loop pump is ineffective in terms of regulating the mass transfer due to its competing effects on gas entrainment and riser liquid velocity. It is an object of the present invention to provide a means of decoupling the two competing effects of the loop pump and to provide more effective mass transfer regulation therein, as well as enhanced foam control and lower overall energy consumption. Furthermore, the present invention overcomes disadvantages known in the art and provides the public with new methods for the optimal production of a variety of useful products. Even minor improvements to a gas fermentation process or system for producing one or more products can have a significant impact on the efficiency, and more particularly, the commercial viability, of such a process or system.

SUMMARY OF THE INVENTION

In a first aspect, there is provided a reactor system for fermentation of a gaseous substrate, the system comprising:
  (a) A fermentation vessel comprising a riser section wherein a liquid fermentation broth and the gaseous substrate are flowed concurrently upwards and a downcomer section wherein the liquid fermentation broth and the gaseous substrate are flowed concurrently downward, said riser and downcomer sections connected by substantially horizontal sections and configured such that liquid fermentation broth and gaseous substrate are circulated, using pumping means, in a primary loop from a point near the bottom of the downcomer section, through the riser to an inlet point at the top of the downcomer section;
  (b) A secondary loop comprising an outlet located at a point near the bottom of the riser section, piping means connecting the outlet from the bottom of the riser to an inlet at the top of the riser and pumping means located between the outlet point and inlet point such that fermentation broth and gaseous substrate is circulated from the bottom of the downcomer to the top of the riser section
  (c) At least one gas inlet, configured to direct gaseous substrate into the riser section; and
  (d) At least one gas outlet, configured to allow gas to exit the riser section.

In particular embodiments of the first aspect, the bioreactor is configured for fermentation of a gaseous substrate to produce products comprising at least one acid or alcohol or mixture thereof. In particular embodiments, the gaseous substrate comprises CO and optionally $H_2$. In yet alternative embodiments, the gaseous substrate comprises $CO_2$ and $H_2$.

In particular embodiments of the first aspect, the reactor comprises a primary loop, itself comprised of a riser section and a downcomer section, and a secondary loop. In particular embodiments, the secondary loop removes fermentation broth from the downcomer section of the fermentation vessel. In particular embodiments, the secondary loop removes fermentation broth downstream of the primary loop pump. In particular embodiments, the fermentation broth is withdrawn downstream of the primary loop pump by means of a secondary pump.

In alternative embodiments, the downcomer section of the fermentation vessel comprises a gate valve located upstream of the secondary loop outlet. In this embodiment, fermentation broth can be withdrawn from the downcomer to the secondary loop by restricting the flow of the primary loop using the gate valve. By adjusting the opening of the gate valve, the pressure downstream of the loop pump but upstream of the gate valve can be regulated to provide a desired secondary loop flow rate. In certain embodiments, pressure in the downcomer is monitored by a pressure gauge. This configuration eliminates the requirement of a secondary loop pump.

In particular embodiments, fermentation broth withdrawn from the downcomer section is circulated via the secondary loop to the top of the fermentation vessel. In particular embodiments, the fermentation broth and gaseous substrate is circulated via the secondary loop from the lower portion of the downcomer section to the top of the riser section. In particular embodiments, the fermentation broth exits the secondary loop from at least one nozzle at the top of the fermentation vessel. In use, the at least one nozzle sprays circulated fermentation broth into the head space of the fermentation vessel. In particular embodiments, circulated fermentation broth is sprayed into the head space by multiple nozzles. In particular embodiments, the at least one nozzle is a shower head. In particular embodiments, the velocity of the liquid jet or jets exiting the nozzle or nozzles can vary from about 0.5 m/s or to about 5 m/s. In use, the liquid jet or jets covers at least a portion of the cross-sectional area of the head space. Under typical fermentation conditions a foam layer exists in the headspace of the fermentation vessel. In certain embodiments, circulated fermentation broth is sprayed into the headspace in order to break up larger bubbles in the foam. This process results in smaller bubbles that are more effectively entrained to the downcomer section, which increases the gas holdup in the downcomer section.

In a particular embodiment, the secondary loop is integrated with a cell recycle system. In this embodiment, the driving force for the secondary loop is derived from the cell recycle pump. In a particular embodiment, the fermentation broth is withdrawn into the secondary loop downstream of the cell recycle module. In particular embodiments, the flow rate of the secondary loop and the pressure of the cell recycle system is regulated by at least one control valve upstream of the cell recycle module.

In a second aspect of the invention, there is provided a method for improving mass transfer of a gaseous substrate to a fermentation broth in a fermentation vessel comprising a riser section wherein a liquid fermentation broth and the gaseous substrate are flowed concurrently upwards and a downcomer section wherein the liquid fermentation broth and the gaseous substrate are flowed concurrently downward, the method comprising:
  (a) providing a gaseous substrate to the fermentation vessel comprising a liquid nutrient medium and one or more microorganism;
  (b) fermentating the gaseous substrate to produce a fermentation broth;
  (c) circulating fermentation broth and a gaseous substrate concurrently upward through the riser section and concurrently downward through the downcomer section of the fermentation vessel; and
  (d) removing at least a portion of the fermentation broth from the bottom of the downcomer section and circulating to the top of the riser section via a secondary loop, wherein the fermentation broth enters the top of the riser section via at least one nozzle.

In a third aspect of the invention, there is provided a method for reducing foam in the headspace of a fermentation vessel comprising a riser section wherein the liquid fermentation broth and the gaseous substrate are flowed concurrently upward and a downcomer section wherein the liquid fermentation broth and the gaseous substrate are flowed concurrently downward, the method comprising:

(a) providing a gaseous substrate to the fermentation vessel comprising a liquid nutrient medium and one or more microorganism;

(b) fermenting the gaseous substrate to produce a fermentation broth and foam present in the headspace of the fermentation vessel;

(c) removing fermentation broth from the downcomer section of the fermentation vessel; and (d) circulating the fermentation broth to the top of the riser section via a secondary loop, wherein the fermentation broth enters the headspace via at least one nozzle;

wherein the fermentation broth entering the headspace reduces foam present within the fermentation vessel.

In a fourth aspect, there is provided a method of producing products by fermentation of a gaseous substrate, the method comprising:

(a) providing the gaseous substrate to a reactor comprising at least a riser section and a downcomer section, the reactor containing liquid nutrient media and a culture of one or more microorganisms, to provide a fermentation broth;

(b) circulating the fermentation broth and gaseous substrate concurrently upward through the riser section and then downward through the downcomer section;

(c) removing at least a portion of the fermentation broth from the downcomer section and passing it to the top of the riser section; and (d) anaerobically fermenting the culture in the reactor to produce one or more products from said substrate.

In particular embodiments of the second, third, and fourth aspects, the reactor is configured as described in the first aspect. In particular embodiments, the method allows for increased mass transfer of a gas to liquid phase in a gas fermentation process. In particular embodiments, the addition of a secondary loop to a circulated loop reactor substantially increases mass transfer.

In particular embodiments, the fermentation broth and gaseous substrate is cycled through a riser section and a downcomer section of a circulated loop reactor. In particular embodiments, the gas stream is input at the bottom of the riser section of the reactor. In alternative embodiments, the gas is input at multiple sites throughout the riser section of the reactor. In alternative embodiments, the gas is input at multiple sites throughout the downcomer section of the reactor.

In particular embodiments, a portion of fermentation broth is withdrawn from near the bottom of the downcomer section of the reactor and circulated to the headspace of the riser section of the reactor. In particular embodiments, the portion of fermentation broth removed from the downcomer is sprayed into the headspace of the riser via a showerhead or perforated nozzle. In certain embodiments, the liquid sprayed into the headspace reduces the foam layer at the top of the liquid contained in the riser. In further embodiments, the liquid sprayed into the headspace breaks foam bubbles and entrains the gas into the fermentation broth of the primary loop of the reactor.

In particular embodiments, one or more microorganisms ferment a carbon containing substrate to produce products including acid(s) and alcohol(s). In particular embodiments, the one or more microorganisms produce one or more products by fermentation of a gaseous substrate comprising CO. In particular embodiments, the fermentation is anaerobic fermentation. In particular embodiments, the one or more microorganism cultures convert CO and optionally $H_2$ to products including acid(s) and/or alcohol(s). In particular embodiments, the products are selected from the group consisting of ethanol, acetic acid, 2,3-butanediol, butanol, lactate, succinate, methyl ethyl ketone (MEK), propanediol, 2-propanol, isopropanol, acetoin, iso-butanol, citramalate, butadiene, poly lactic acid, isobutylene, 3-hydroxy propionate (3HP), acetone, fatty acids and mixtures thereof.

In various embodiments, the fermentation is carried out using a microorganism culture comprising one or more strains of carboxydotrophic bacteria. In various embodiments, the carboxydotrophic bacterium is selected from *Clostridium, Moorella, Oxobacter, Peptostreptococcus, Acetobacterium, Eubacterium,* or *Butryribacterium*. In one embodiment, the carboxydotrophic bacterium is *Clostridium autoethanogenum*. In particular embodiments, the bacterium has the identifying characteristics of accession number DSMZ10061 or DSMZ23693.

The gaseous substrate may comprise a gas obtained as a by-product of an industrial process. In certain embodiments, the industrial process is selected from the group consisting of ferrous metal products manufacturing, non-ferrous products manufacturing, refinery processes, petroleum refining processes, gasification of biomass, gasification of coal, electric power production, carbon black production, ammonia production, methanol production and coke manufacturing. Alternatively, the gaseous substrate is a reformed gas source including natural gas, shale gas, associated petroleum gas and biogas. In alternative embodiments, the gas is obtained by gasification of biomass or municipal solid waste. In one embodiment of the invention, the gaseous substrate is syngas. In one embodiment, the gaseous substrate comprises a gas obtained from a steel mill.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

The invention will now be described in detail with reference to the accompanying Figures in which.

DETAILED DESCRIPTION OF THE INVENTION

Definitions

Figure 1:
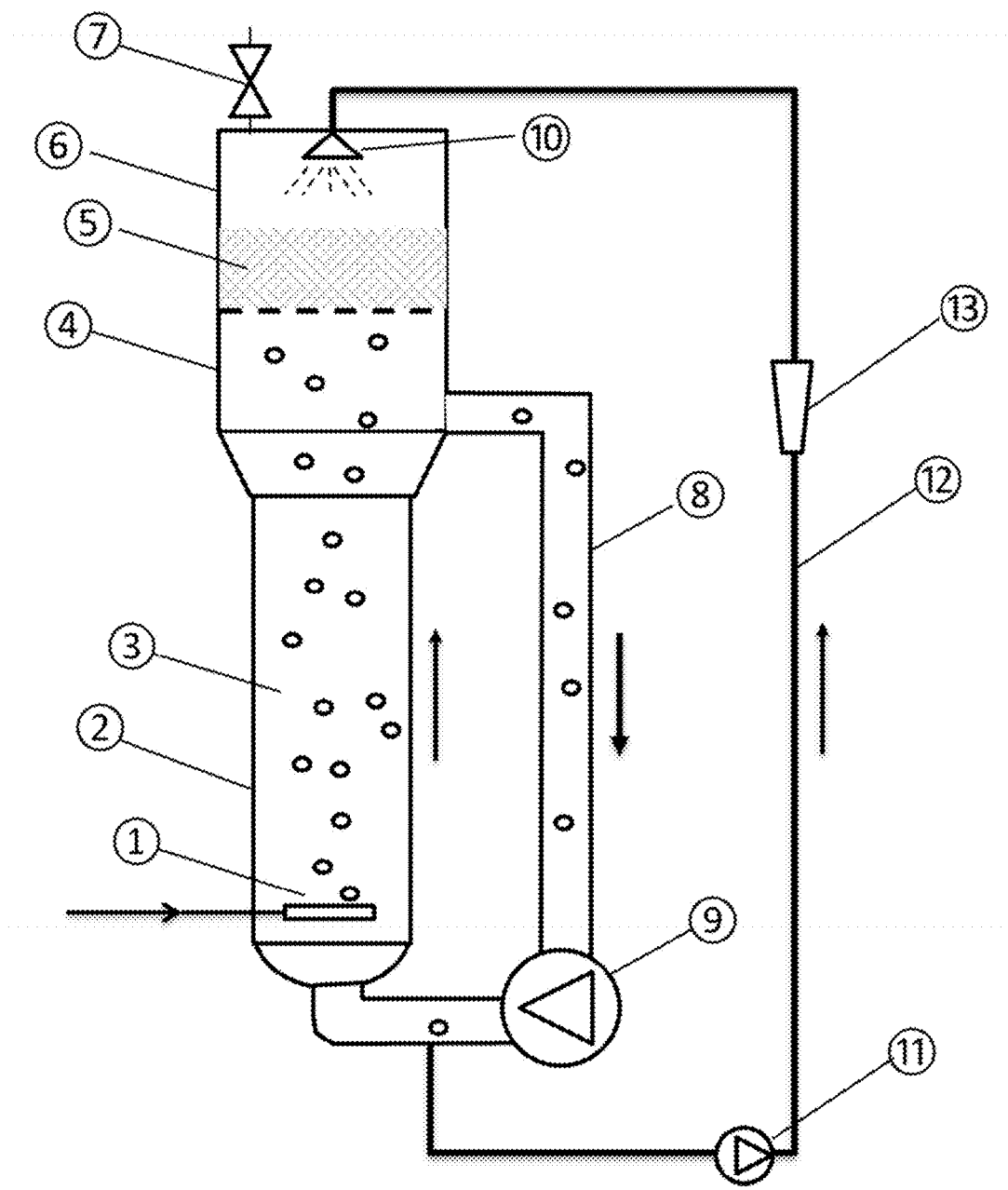
FIG. 1 shows a schematic diagram of an embodiment of a circulated loop reactor comprising a secondary loop.

Unless otherwise defined, the following terms as used throughout this specification are defined as follows:

The term "gaseous substrate" includes any gas which contains a compound or element used by a microorganism as a carbon source and optionally energy source in fermentation. The gaseous substrate will typically contain a significant proportion of CO, preferably at least about 5% to about 100% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise a ratio of about 2:1, or 1:1, or 1:2 ratio of $H_2$:CO. In particular embodiments, the substrate may comprise a ratio of between 2:1 to 1:2 of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

The term "liquid nutrient media" includes a liquid medium comprising nutrients suitable for fermentation of one or more microorganisms. The liquid nutrient media will contain vitamins and/or minerals sufficient to permit growth of the micro-organism(s) used. Anaerobic media suitable for fermentation using CO are known in the art. For example, suitable media are described in Beibel (Journal of Industrial Microbiology & Biotechnology (2001) 27, 18-26).

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The terms "fermentation vessel", "reactor" and/or "bioreactor" include devices and vessels for gas/liquid contact, suitable for conducting a desired fermentation.

A "forced-circulation external-loop reactor" and/or "circulated loop reactor" comprises a vessel usually having two vertical cylinders with horizontal connections between them. the content, which is usually a liquid plus a gas substrate is forced to circulate upward from one vertical cylinder (riser) through a horizontal connection then downward through the other vertical cylinder (downcomer) and then through a lower horizontal connection of the reactor by an impeller or a pump of an appropriate type to complete the loop.

The term "riser" comprises a section of a reactor where the liquid/gas content travels concurrently upwards.

The term "downcomer" comprises a section of a reactor where the liquid/gas content travels concurrently downwards.

A term "separator" includes the part of a reactor where at least a portion of the gas separates from the gas-liquid two phase mixture by allowing the bubbles to rise to the surface of the liquid.

The "headspace" includes the part of a reactor above the separator defined above.

The term "loop pump" comprises a pump that is used to drive the liquid medium in the reactor to flow. The liquid medium may contain a certain portion of gas bubbles or dissolved gas. In a particular embodiment, it can include an axial flow pump installed at the bottom of the downcomer.

The term "sparger" and/or "gas distributor" comprises a device to introduce gas into a liquid to agitate it or to dissolve the gas in the liquid. In a particular embodiment, the sparger may be a perforated plate, sintered glass, sintered steel, porous rubber pipe, porous metal pipe, porous ceramic or stainless steel. The sparger may be of various grades (i.e., porosities) to provide a specific sized "bubble".

The term "nozzle" and/or "showerhead" comprises a device that splits a liquid flow into multiple liquid jets. In a particular embodiment, the nozzle is a perforated pipe with down-facing pores.

As referred to herein, "foam" is a mass of bubbles of gas in a matrix of liquid films. The volumetric gas fraction in foam is preferably higher than 70%.

The "conversion" of a substrate is the ratio of a substrate reacted during a reaction to the total amount of the substrate supplied to the reactor.

The term "gas holdup" includes the volumetric gas fraction in a gas-liquid two-phase mixture.

The term "mass transfer" used herein predominantly means the transfer of gaseous substrates into the liquid medium where the microorganism reside.

The term "mass transfer efficiency", "volumetric mass transfer efficiency" and the like, refers to the rate of the dissolution of a gaseous substrate into the liquid medium per unit time per unit reactor volume.

The terms "increasing the efficiency", "increased efficiency" and the like, when used in relation to a mass transfer process, refer to a higher rate of dissolution of the gaseous substrate into the liquid medium.

Unless the context requires otherwise, the phrases "fermenting", "fermentation process" or "fermentation reaction" and the like, as used herein, are intended to encompass both the growth phase and product biosynthesis phase of the process.

Efficient fermentation of gaseous substrates to produce products requires control of the amount of substrate transferred into a fermentation broth to ensure high rates of production of desired products and the prevention of inhibition. In addition, in order to maximise carbon capture, the amount of a substrate transferred into a fermentation broth, such that it can be converted into products by one or more micro-organisms, must be maintained at a high level. Furthermore, in order to maintain overall efficiency, the substrate should be transferred into solution such that power input across the system is minimised.

In accordance with the invention, there is provided a system for improved fermentation of a gaseous substrate through the introduction of a secondary loop to a conventional forced-circulation external loop reactor. The reactor comprises a primary loop through which fermentation broth comprising a gaseous substrate is circulated through a riser segment and a downcomer section by a loop pump. Downstream of the loop pump a portion of fermentation broth is withdrawn from the downcomer section and is directed to the top of the reactor via a secondary loop. In particular embodiments, the portion of the fermentation broth removed from the primary loop is sprayed from the secondary loop via a nozzle.

The primary rate-limiting step in gas fermentation is the gas-to-liquid mass transfer. Known means of increasing mass transfer are through agitation of the gas-liquid mixture, such as mechanical stirring of the broth. However, these known methods for increasing mass transfer require a large power input, which becomes inefficient and/or uneconomical as scale increases.

The reactor of the present invention is configured as to significantly improve mass transfer of a gas phase to a liquid phase. In particular embodiments, a portion of liquid flow is withdrawn from the discharge of the loop pump in the downcomer section, and therefore the volumetric liquid flow rate in the riser section is less than that of the downcomer section. In certain embodiments, the withdrawal of a portion of fermentation broth from the downcomer section results in increased gas hold up and mass transfer in the riser section of the reactor.

In a particular embodiment of an apparatus of the invention, the reactor consists of a riser section and a downcomer section. The riser and downcomer are connected by two horizontal sections at each end to form a primary loop, and liquid/gas flow through is driven through the primary loop at least partly by a pump at the bottom of the downcomer. In particular embodiments, the gas is introduced into the system via an appropriate type of sparger. In particular embodiments, a secondary loop line connects the bottom of the downcomer and the top of the reactor to form a secondary loop. In particular embodiments, the secondary loop line is connected to the downcomer downstream of the primary loop pump but before the riser. In particular embodiments, the secondary loop line withdraws a stream of liquid from the discharge of the loop pump by a secondary pump. In particular embodiments, a liquid stream is passed to the top of the reactor via the secondary loop line, where the liquid is sprayed into the headspace of the reactor via at least one nozzle. In certain embodiments, the at least one nozzle is a shower head.

In embodiments of the invention, the system has application in the fermentation of gaseous substrates to one or more products, said products including acids, alcohols and diols. In particular, ethanol, acetic acid and 2,3-butanediol are produced by fermentation of a gaseous substrate comprising CO. Alternative products include butanol, lactate, succinate, methyl ethyl ketone (MEK), propanediol, 2-propanol, isopropanol, acetoin, iso-butanol, citramalate, butadiene, poly lactic acid, isobutylene, 3-hydroxy propionate (3HP), acetone, fatty acids and mixtures thereof.

Typically, the headspace of the riser section of the reactor comprises a foam layer resulting from rising gas and agitation of the broth. The present invention allows for fermentation broth used in the fermentation process in the reactor to be sprayed onto the foam layer, wherein the spray has the effect of breaking up large gas bubbles in the foam. Larger gas bubbles rise with higher velocity through the liquid, and therefore have a shorter residence time in the riser, with lower mass transfer of the contained gas. Through breaking the larger gas bubbles, the smaller bubbles are entrained back into the downcomer section of the reactor, which provides further opportunity for mass transfer. In a further embodiment, the shower is sprayed on the foam layer in the headspace to effectively collapse the foam, in order that it does not accumulate and block the pipelines downstream of the reactor.

In a further embodiment, the shower turns the foam layer into a counter current gas-liquid contactor where the liquid flows downwards and the gas flows upwards. The mass transfer efficiency in this counter-current flow itself is high due to the counter-current action and the high gas content. Although the gaseous substrate concentration in the gas phase may be lean, this part of the reactor will contribute a significant amount to substrate uptake. When there are fluctuations in the gas supply, the height of the foam later can be adjusted accordingly to maintain a stable production rate.

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first growth reactor in which the micro-organisms are cultured, and one or more production fermentation reactors configured in series or in parallel, to which fermentation broth from the growth reactor may be fed and in which most of the fermentation product (e.g. ethanol and acetate) may be produced. The bioreactor of the present invention is adapted to receive a CO and/or $H_2$, or $CO_2$ and/or $H_2$ containing substrate.

In particular embodiments, the gas inlet is situated at the bottom of the riser section of the reactor. The inventors have identified that an excess of CO in the area near the gas inlet (i.e., the bottom of the riser) results in inhibition of the microorganism. However, this problem is surprisingly overcome by the present invention. In particular embodiments, the gas entrained in the headspace of the riser section of the reactor comprises a lower CO content than the fresh inlet gas at the bottom of the riser. When the entrained gas is eventually recycled through the downcomer to return to the bottom of the riser, the entrained gas mixes with the fresh inlet gas and reduces the dissolved CO concentration at the bottom of the riser, effectively reducing the chance of substrate inhibition, and improving the overall CO conversion. The same problem can also be resolved by splitting the feed gas into more than one streams and inject them at multiple sites of the riser and downcomer of the reactor. The latter method however does not significantly improve CO conversion.

In accordance with particular embodiments, the mass transfer rate of the gaseous substrate to the microbial culture can be controlled such that the microbial culture is supplied with substrate at or towards an optimum supply rate. In the reactors, the mass transfer rate can be controlled by controlling partial pressure of the gas substrate and/or by controlling the liquid flow-rate or gas holdup. In particular embodiments, the mass transfer is controlled by controlling the rate at which fermentation broth is pumped through both the primary and secondary loop of the reactor.

In particular embodiments, the fresh gas is introduced into the vessel by one or more gas inlets. Typically, high mass transfer can be achieved by introducing the gaseous substrate as fine bubbles. Those skilled in the art will appreciate means for introducing gaseous substrate, such as spargers. In particular embodiments, the gas is introduced into the vessel by fine bubble diffusers or other type of fine bubble generators.

Upon consideration of the instant disclosure, those skilled in the art will appreciate the size and type of pumps required to circulate fermentation broth comprising one or more microorganisms around both the primary and secondary loops. It must be noted that the higher the gas hold up in the liquid, the less dense the liquid, so the pump needs to be configured to circulate liquids of varying densities as the composition of the gas/liquid slurry changes. By way of non-limiting example, one or more multiphase pumps configured for pumping the fermentation broth/gas slurry can be used to circulate single phase liquids and increase the discharge pressure of a fluid. Using a rotating impeller, liquid enters the pump along the rotating shaft of the motor and accelerates the liquid radially outward through a diffuser chamber. Centrifugal pumps can also operate with lower two phase gas holdups without cavitating (a known vulnerability of centrifugal pumps), by maintaining an adequate net positive suction head. Those skilled in the art will appreciate there are multiphase pumping solutions available for large scale applications.

In alternative embodiments, the downcomer section of the fermentation vessel comprises a gate valve located upstream of the secondary loop outlet. In this embodiment, fermentation broth can be withdrawn from the downcomer to the secondary loop by restricting the flow of the primary loop using the gate valve. By adjusting the opening of the gate valve, the pressure downstream of the loop pump but upstream of the gate valve can be regulated to provide a desired secondary loop flow rate. In certain embodiments, pressure in the downcomer is monitored by a pressure gauge. This configuration eliminates the requirement of a secondary loop pump.

In particular embodiments, the secondary loop is integrated with a cell recycle system. The cell recycle system provides a means to separate microorganisms from permeate in order that the microorganisms are returned to the reactor for further fermentation. A cell recycle module continuously draws broth permeate, while retaining cells. Those skilled in the art would understand that cell recycle members may include, but are not limited to, cell recycle membranes or disc-stack centrifugal separators. In preferred embodiments, cells are retained in the fermentation broth using ultrafiltration. In certain embodiments, the driving force for the secondary loop is derived from the cell recycle pump. In preferred embodiments, the cell recycle pump is much larger than the secondary loop pumps described above. In a particular embodiment, the fermentation broth is withdrawn into the secondary loop downstream of the cell recycle module. In particular embodiments, the flow rate of the secondary loop and the pressure of the cell recycle system is regulated by at least one control valve upstream of the cell recycle module. In particular embodiments, the flow rate of the secondary loop is regulated by two control valves upstream of the cell recycle module. The first control valve regulates flow to the top of the reactor via the secondary loop line. The second control valve regulates flow to a separate line that returns fermentation broth to the downcomer. In certain embodiments, in order to increase the flow rate of the secondary loop, the flow through first control valve is increased and the flow through the second control valve is restricted. In order to decrease the flow rate of the secondary loop, the flow through the first control valve is restricted and the flow through the second control valve is increased. In order that cell recycle flow requirements are met, the two control valves are configured to maintain a constant flow rate through the cell recycle module.

The reactor of the present invention may additionally include a wide range of suitable gas/liquid contact modules that can provide effective mass transfer of a gaseous substrate necessary to improve the efficiency of microbial fermentations. A contact module provides a unique geometrical environment allowing gas and liquid to mix thoroughly along a set flow path, causing the entrained gas to dissolve in the liquid more uniformly. By way of example, these contact modules include, but are not limited to, a matrix of structured corrugated metal packing, random packing, sieve plates and static mixers, all of which have a range of well-known types and densities and are widely commercially available.

Various embodiments of systems of the invention are described in the accompanying Figures.

FIG. 1 is a schematic diagram of an embodiment of a circulated loop reactor comprising a secondary loop. The reactor consists of a riser (2), where the liquid and gas mixture (3) flow concurrently upwards, and a downcomer (8), where the liquid and gas flows concurrently downwards. The riser (2) and downcomer (8) are connected by two horizontal sections at each end and the two-phase flow is driven at least partly by a pump (9) at the bottom of the downcomer (8). The gas is introduced into the system via one or more appropriate type of spargers (1). A portion of the gas is carried over into the downcomer (8) by the liquid flow at the gas-liquid separator (4), and this portion of the gas is referred to as the "entrained gas" or the "recycled gas" herein. The non-entrained gas leaves the system via a control valve (7), after passing the headspace (6). Typically, there is a foam layer (5) of some height above the liquid level in the headspace (6). It can be seen from this diagram that the liquid and gas mixture flows from the riser (2) to the downcomer (8) and back forming a loop (i.e., the primary loop).

The secondary loop circulates fermentation broth (3) from the bottom of the downcomer (8) to the top of the reactor. Downstream of the primary loop pump (9) but before the riser (2), a stream of liquid is withdrawn from the discharge of the loop pump (9) by a secondary pump (11). The stream is passed to the top of the reactor via the secondary loop line (12), where the liquid is sprayed in the headspace (6) via an appropriate spray nozzle or shower head (10). The liquid is sprayed on to the surface of the foam layer (5) at a velocity from about 0.5 m/s to about 5 m/s in order to break up the foam. The liquid flow rate of the secondary loop is measured and monitored by a flow meter (13).

Figure 2:
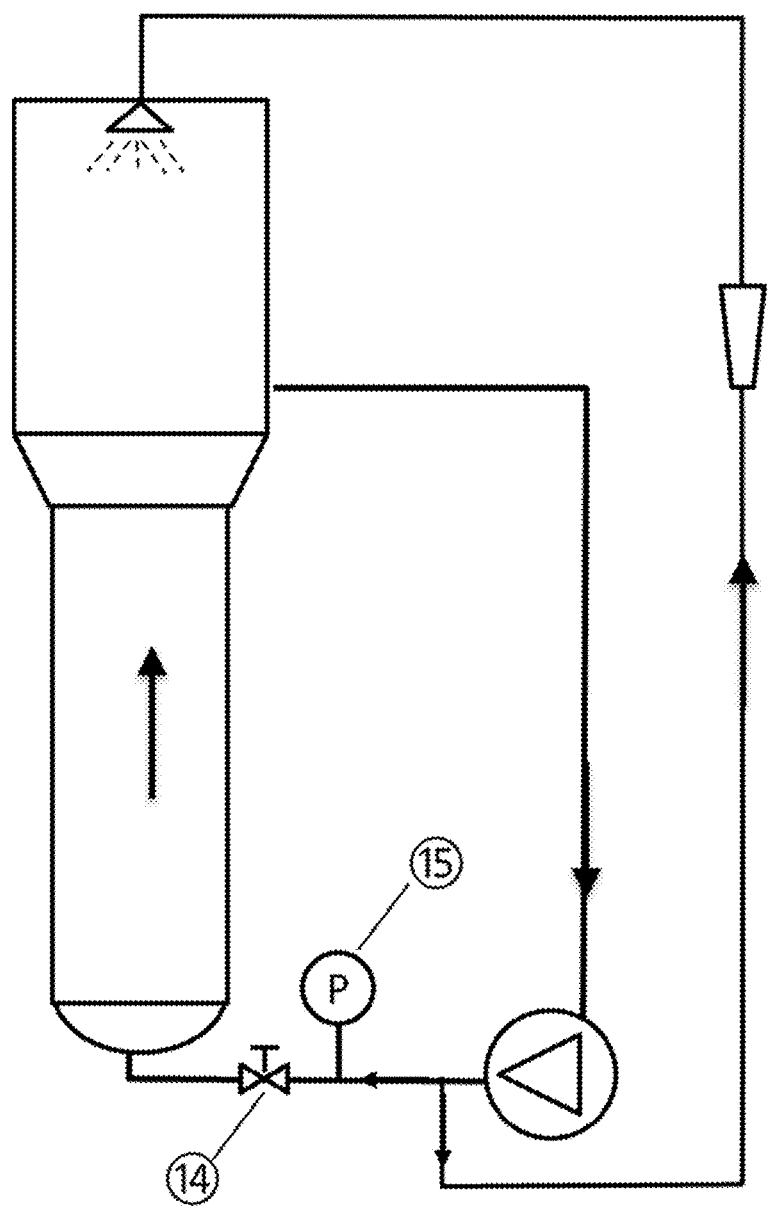
FIG. 2 shows a schematic diagram of an alternative embodiment of the circulated loop reactor comprising a gate valve, eliminating the need for a secondary pump.

FIG. 2 shows a schematic diagram of an alternative embodiment of the circulated loop reactor comprising a gate valve (14). Other components of the reactor are removed from the figure for the sake of clarity. By adjusting the opening of the gate valve, the pressure downstream of the loop pump, but upstream of the gate valve, can be regulated to give a desired secondary loop flow rate. The pressure is monitored by a pressure gauge (15). This configuration eliminates the requirement for a secondary loop pump.

Figure 3:
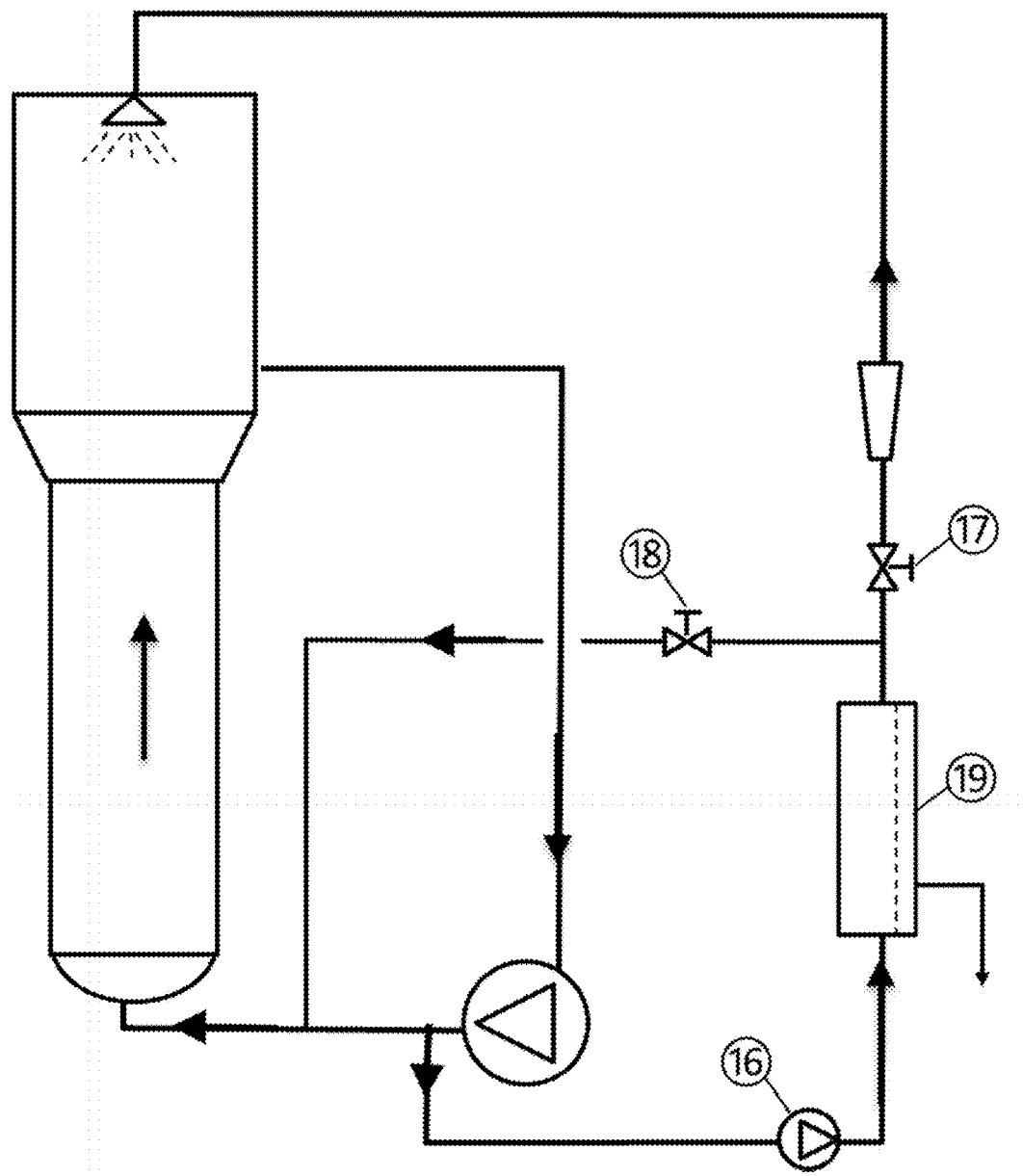
FIG. 3 shows a schematic diagram of an alternative embodiment of the circulated loop reactor comprising an integrated cell recycle system, eliminating the need for a secondary pump.

FIG. 3 shows a schematic diagram of an alternative embodiment of the circulated loop reactor comprising an integrated cell recycle system. Other components of the reactor are removed from the figure for the sake of clarity. In this embodiment, the secondary loop is withdrawn downstream of a cell recycle module (19), wherein the driving force for the secondary loop comes from the cell recycle pump (16). In preferred embodiments, the cell recycle pump is much larger than the secondary loop pumps described above. In particular embodiments, the cell recycle module separates cells from permeate using ultrafiltration or other separation means such as membranes. Only a portion of fermentation broth provided to the cell recycle module is passed to the top of the reactor, and therefore the flow rate of the secondary loop and the pressure of the cell recycle system are regulated by two control valves (17, 18) downstream of the cell recycle module (19). The first control valve (17) regulates flow to the top of the reactor via the secondary loop line. The second control valve (18) regulates flow to a separate line that returns fermentation broth to the downcomer. In certain embodiments, in order to increase the flow rate of the secondary loop, the flow through first control valve (17) is increased and the flow through the second control valve (18) is restricted. In order to decrease the flow rate of the secondary loop, the flow through the first control valve (17) is restricted and the flow through the second control valve (18) is increased. In order that cell recycle flow requirements are met, the two control valves (17, 18) are configured to maintain a constant flow rate through the cell recycle module (19).

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

Fermentation

Processes for the production of ethanol and other alcohols from gaseous substrates (such as those described in the background section above) are known. Exemplary processes include those described for example in WO 2007/117157 and WO 2008/115080, as well as U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

In one embodiment, the microorganism is selected from the group of carboxydotrophic Clostridia comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*. In a further embodiment, the microorganism is from the cluster of carboxydotrophic Clostridia comprising the species *C. autoethanogenum*, *C. ljungdahlii*, and *C. ragsdalei* and related isolates. These include but are not limited to strains *C. autoethanogenum* JAI-1T (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETCT (DSM13528=ATCC 55383) (Tanner, Miller, & Yang, 1993), *C. ljungdahlii* ERI-2 (ATCC 55380) (U.S. Pat. No. 5,593, 886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11T (ATCC BAA-622) (WO 2008/028055), related isolates such as "*C. coskatii*" (US20110229947) and "*Clostridium* sp." (Tyurin & Kiriukhin, 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of the above-referenced cluster have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini et al., 1994; Köpke et al., 2011; Tanner et al., 1993) (WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al., 2011). Also reduction of carboxylic acids into their corresponding alcohols has been shown in a range of these organisms (Perez, Richter, Loftus, & Angenent, 2012). These traits are therefore not specific to one organism like *C. autoethanogenum* or *C. ljungdahlii*, but rather general traits for carboxydotrophic, ethanol-synthesizing Clostridia and it can be anticipated that mechanism work similar across these strains, although there may be differences in performance (Perez et al., 2012).

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSM 10061.

The fermentation may be carried out in any suitable bioreactor. In some embodiments of the invention, the bioreactor may comprise a first, growth reactor in which the micro-organisms are cultured, and one or more subsequent production fermentation reactors configured in parallel or in series, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as is conducted in a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Alternatively, the gaseous substrate is a reformed gas source including natural gas, shale gas, associated petroleum gas and biogas. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

The CO-containing gaseous substrate will ideally contain a significant proportion of CO, such as at least 5% to about 100% CO by volume, or from 20% to 95% CO by volume, or from 40% to 95% CO by volume, or from 60% to 90% CO by volume or from 70% to 90% CO by volume. Gaseous substrates having lower concentrations of CO, such as 6%, may also be appropriate, particularly when $H_2$ and $CO_2$ are also present.

While it is not necessary for the gaseous substrate to contain any hydrogen, the presence of hydrogen will generally not be detrimental to product formation in accordance with methods of the invention. However, in certain embodiments of the invention, the gaseous substrate is substantially hydrogen free (less than 1%). The gaseous substrate may also contain some $CO_2$, such as about 1% to about 30% by volume, or such as about 5% to about 10% $CO_2$.

As noted previously, the presence of hydrogen in the substrate stream can lead to an improvement in efficiency of overall carbon capture and/or ethanol productivity. For example, WO0208438 describes the production of ethanol using gas streams of various compositions.

Accordingly, it may be necessary to alter the composition of the substrate stream in order to improve alcohol production and/or overall carbon capture. Additionally or alternatively, the composition may be altered (i.e. CO, $CO_2$ and/or $H_2$ levels adjusted) to optimise the efficiency of the fermentation reaction and ultimately improve alcohol production and/or overall carbon capture.

In some embodiments, the CO-containing gaseous substrate may be sourced from the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e. partially combusted with oxygen, to produce synthesis gas (syngas comprising significant amounts of $H_2$ and CO). Gasification processes typically produce a synthesis gas with a molar ratio of $H_2$ to CO of about 0.4:1 to 1.2:1, together with lesser amounts of $CO_2$, $H_2S$, methane and other inert substances. The ratio of the gas produced can be varied by means known in the art and are described in detail in WO200701616. However, by way of example, the following gasifier conditions can be altered to adjust the $CO:H_2$ product ratio: feedstock composition (particularly C:H ratio), operating pressure, temperature profile (influencing quench of product mix) and oxidant employed (air, oxygen enriched air, pure $O_2$ or steam; wherein steam tends to result in higher $CO:H_2$ ratios). Accordingly, the operating conditions of the gasifier can be adjusted to provide a substrate stream with a desirable composition for fermentation or blending with one or more other streams to provide an optimised or desirable composition for increased alcohol productivity and/or overall carbon capture in a fermentation process.

In other embodiments, the substrate comprising CO can be derived from the steam reforming of hydrocarbons. Hydrocarbons, such as natural gas hydrocarbons can be reformed at high temperature to yield CO and $H_2$ according to the following:

$$C_nH_m + nH_2O \rightarrow nCO + (m/2+n)H_2$$

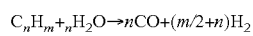

By way of example, steam methane reforming involves reacting steam with methane to produce CO and $H_2$ at elevated temperature (700-1100° C.) in the presence of a nickel catalyst. The resulting stream (comprising 1 mol CO and 3 mol $H_2$ for every mol $CH_4$ converted) can be passed directly to the fermenter or blended with a substrate stream from another source to increase ethanol productivity and/or overall carbon capture in a fermentation process. Alcohols such as methanol can also be reformed to produce $CO_2$ and $H_2$ that may be used in a similar manner.

In another embodiment, the substrate comprising CO is derived from the steel manufacturing process. In the steel making process, iron ore is crushed and pulverised, subjected to pre-treatments such as sintering or pelletizing, and then passed to a blast furnace (BF), where it is smelted. In the smelting process, coke serves as the source of carbon, which works as a reducing agent to reduce the iron ore. Coke acts as the heat source for heating and melting the materials. The hot metal is decarburised in a basic oxygen furnace (BOF) by injecting a high-velocity jet of pure oxygen against the surface of the hot metal. The oxygen reacts directly with carbon in the hot metal to produce carbon monoxide (CO). Thus, a gas stream with a high CO content is exhausted from the BOF. According to certain embodiments of the invention, this stream is used to feed one or more fermentation reactions. However, as would be apparent to one of skill in the art, CO may be produced elsewhere within the steel making process, and according to various embodiments of the invention, such alternative sources may be used instead of or in combination with exhaust gases from the BOF. Depending on the source (i.e., the particular stage within the steel making process), the CO content of the gases exhausted thereby may vary. Also, there may be periods when there are breaks in one or more of such streams, particularly in batch processing plants.

Typically, streams exhausted from the steel mill decarburisation process comprise a high concentration of CO and low concentrations of $H_2$. While such streams can be directly passed to the bioreactor with little or no further treatment, it may be desirable to optimise the composition of the substrate stream in order to achieve higher efficiency of alcohol production and/or overall carbon capture. For example, the concentration of $H_2$ in the substrate stream may be increased before the stream is passed to the bioreactor.

According to particular embodiments of the invention, streams from two or more sources can be combined and/or blended to produce a desirable and/or optimised substrate stream. For example, a stream comprising a high concentration of CO, such as the exhaust from a steel mill converter, can be combined with a stream comprising high concentrations of $H_2$, such as the off-gas from a steel mill coke oven.

Alternatively or additionally, an intermittent stream comprising CO, such as an exhaust stream from the converter, may be combined with and/or blended with a substantially continuous stream comprising CO and optionally $H_2$, such as syngas produced in a gasification process as described previously. In certain embodiments, this would maintain the provision of a substantially continuous substrate stream to the bioreactor. In a particular embodiment, the stream produced by the gasifier may be increased and/or decreased in accordance with the intermittent production of CO from an industrial source in order to maintain a substantially continuous substrate stream with a desirable or optimised composition. In another embodiment, the gasifier conditions may be altered as described previously in order to increase or decrease the $CO:H_2$ ratio, in accordance with the intermittent production of CO from an industrial source, in order to maintain a substantially continuous substrate stream with a desirable or optimised CO and $H_2$ composition.

Typically, the substrate streams used in the invention will be gaseous; however, the invention is not limited thereto. For example, the carbon monoxide may be provided to a bioreactor in a liquid. For example, a liquid may be saturated with a carbon monoxide containing gas and then that liquid added to a bioreactor. This may be achieved using standard methodology. By way of example, a microbubble dispersion generator (Hensirisak et. al., Scale-up of microbubble dispersion generator for aerobic fermentation; Applied Biochemistry and Biotechnology Volume 101, Number 3, October, 2002) could be used for this purpose.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080, referred to above. The "Examples" herein provide other exemplary media.

The fermentation should desirably be carried out under appropriate conditions for the desired fermentation to occur (e.g. CO-to-alcohol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it may be preferable that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, because a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080 and U.S. Pat. Nos. 6,340,581, 6,136,577, 5,593,886, 5,807,722 and 5,821,111. However, briefly and by way of example only, ethanol may be recovered from the fermentation broth by methods such as fractional distillation or evaporation, and extractive fermentation.

Distillation of ethanol from a fermentation broth yields an azeotropic mixture of ethanol and water (i.e. 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. In this process, oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the non-volatile oleyl alcohol is recovered for re-use in the fermentation.

Acetate may also be recovered from the fermentation broth using methods known in the art. For example, an adsorption system involving an activated charcoal filter may be used. In this case, microbial cells are typically first removed from the fermentation broth using a suitable separation method. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth be reduced to less than about 3 before it is passed through the activated charcoal column, to convert the majority of the acetate to the acetic acid form.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more products from the broth simultaneously or sequentially. Ethanol may conveniently be recovered by distillation, and acetate may be recovered by adsorption on activated charcoal, using the methods described above. The separated microbial cells can be returned to the fermentation bioreactor. The cell free permeate remaining after the ethanol and acetate have been removed can also be returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Industrial Off Gas as a Resource for Fermentation

In accordance with other aspects of the invention, industrial waste gases are used in a fermentation reaction with no or only minimal additional scrubbing or pre-treatment steps being used to make the gases suitable therefor.

The waste gases may result from any number of industrial processes. The invention has particular applicability to supporting the production of ethanol from gaseous substrates such as high volume CO-containing industrial flue gases. Examples include gases produced during ferrous metal products manufacturing, non-ferrous products manufacturing, refinery processes, petroleum refining processes, gasification of coal, gasification of biomass, electric power production, carbon black production, ammonia production, methanol production and coke manufacturing. In certain embodiments the CO containing substrate is derived from gasification of biomass or municipal solid waste. In a particular embodiment of the invention, the waste gases are generated during a process for making steel. For example, those skilled in the art will appreciate the waste gases produced during various stages of the steel making process have high CO and/or $CO_2$ concentrations. In particular, the waste gas produced during the decarburisation of steel in various methods of steel manufacturing, such as in an oxygen converter (e.g. BOF or KOBM), has a high CO content and low $O_2$ content making it a suitable substrate for anaerobic carboxydotrophic fermentation.

Waste gases produced during the carburisation of steel are optionally passed through water to remove particulate matter before passing to a waste stack or flue for directing the waste gas into the atmosphere. Typically, the gases are driven into the waste stack with one or more fans.

In particular embodiments of the invention, at least a portion of the waste gas produced during the decarburisation of steel is diverted to a fermentation system by suitable conduit means. By way of example, piping or other transfer means can be connected to the waste gas stack from a steel mill to divert at least a portion of the waste gas to a fermentation system. Again, one or more fans can be used to divert at least a portion of the waste gas into the fermentation system. In particular embodiments of the invention, the conduit means is adapted to provide at least a portion of the waste gas produced during the decarburisation of steel to a fermentation system. The control of and means for feeding gases to a bioreactor will be readily apparent to those of ordinary skill in the art to which the invention relates.

While steel mills can be adapted to substantially continuously produce steel and subsequently waste gases, particular aspects of the process may be intermittent. Typically the decarburisation of steel is a batch process lasting several minutes to several hours. As such, the conduit means may be adapted to divert at least a portion of the waste gas, such as the gas produced during the decarburisation of steel, to the fermentation system if it is determined the waste gas has a desirable composition.

The pH of the contents of the bioreactor used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilising *Clostridium autoethanogenum*, the pH may be adjusted to approximately 5.5 to 6.5, most preferably to approximately 5.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as $H_2SO_4$ can be used to raise and lower the pH of the fermentation medium and maintain the desired pH.

An additional benefit of the invention is that, because there is no or only minimal scrubbing and/or other treatment processes performed on the waste gases prior to their use in a fermentation reaction, the gases will contain additional material resulting from the industrial process, which additional material may be used, at least in part, as a feedstock for the fermentation reaction.

EXAMPLES

Materials and Methods

TABLE 1

Media composition

| Component | Final concentration mM/L |
|---|---|
| KCl | 25 |
| $CaCl_2 \cdot 2H_2O$ | 2 |
| $MgCl_2 \cdot 6H_2O$ | 2 |
| NaCl | 2 |
| $H_3PO_4$ | 5 |
| Metal solution [Table 2] | 20 mL |
| Vitamin solution [Table 3] | 20 mL |

TABLE 2

Trace metals solution

| Metal | Concentration mM/L stock solution |
|---|---|
| $FeCl_2 \cdot 4H_2O$ | 20 |
| $MnCl_2 \cdot 4H_2O$ | 0.4 |
| $CoCl_2 \cdot 6H_2O$ | 1.0 |
| $ZnCl_2$ | 1.0 |
| $H_3BO_3$ | 1.0 |
| $Na_2MoO_4 \cdot 2H_2O$ | 0.4 |
| $NiCl_2 \cdot 6H_2O$ | 0.4 |
| $Na_2SeO_3$ | 0.4 |
| $Na_2WO_4 \cdot 2H_2O$ | 0.4 |

TABLE 3

Vitamin solution

| Vitamin | Concentration mg/L stock solution (100x) |
|---|---|
| Thiamine hydrochloride (Vitamin B1) | 50 |
| Riboflavin (Vitamin B2) | 50 |
| Nicotinic acid (Niacin or Vitamin B3) | 50 |
| Pantothenic acid (Vitamin B5) | 50 |
| Pyridoxine hydrochloride (Vitamin B6) | 10 |
| Biotin (Vitamin B7) | 20 |
| Folic acid (Vitamin B9) | 20 |
| 4-Aminobenzoic acid (PABA or Vitamin B10) | 50 |
| Cyanocobalamin (Vitamin B12) | 50 |
| Lipoic acid (Thioctic acid) | 50 |

Bacteria:

*Clostridium autoethanogenum* used is that deposited at the German Resource Centre for Biological Material (DSMZ) and allocated the accession numbers DSMZ 19630.

Fermentation:

Media was prepared according to the composition described in Tables 1-3 to a volume of 1.5 L, and 1.5 ml of resazurin added. The solution was heated and agitated while degassed with $N_2$. $ANa_2S$ drip was started at a rate of 0.1 ml/hr and temperature of the bioreactor set to 37° C. The pH was adjusted to 5.0 with $NH_4OH$ and chromium was added to adjust the ORP to −200 mV. The bioreactor was then supplied with RMG (43% CO, 20% $CO_2$, 2.5% $H_2$ and 33% $N_2$).

Experiment 1: Effect of the Secondary Loop on Liquid Flow Rate, Gas Hold Up and CO Conversion The reactor comprised a riser with a diameter of 0.254 m and a downcomer with a diameter of 0.138 m. The reactor comprised a secondary loop of 0.043 m diameter withdrawing broth from the bottom of the downcomer and circulating broth using a mechanical pump to the top of the riser, where the broth entered the headspace of the reactor via a showerhead. The height of the reactor was 6 m. The reactor was tested during continuous fermentation of *Clostridium autoethanogenum*.

Figure 4:
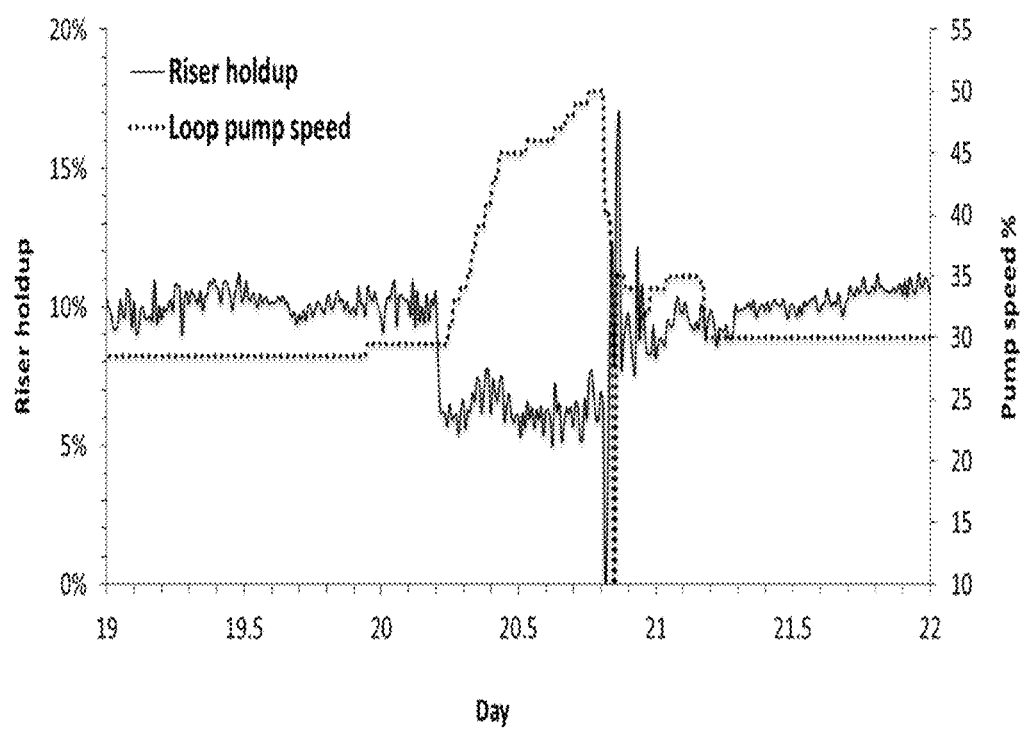
FIG. 4 is a graph displaying the effect of the secondary loop flow rate on the riser holdup based on experimental results from a 6 meter high reactor.

During testing, the liquid flow rate in the downcomer, $Q_{L,0}$ was 30 m³/hr and the liquid flow rate in the second loop $Q_{L,2}$ was 5.5 m³/hr. At around Day 20.02, the secondary loop was turned off and an immediate decrease in riser holdup from 11% to 5% was observed, as shown in FIG. 4. The loop pump speed was increased from 30% to 50% during this period but it can be seen that this did not effectively improve the riser holdup, due to the two competing effects of the loop pump speed on the riser holdup. On Day 20.8, the secondary loop was reactivated and the riser holdup was improved immediately, even at a reduced loop pump speed.

Figure 5:
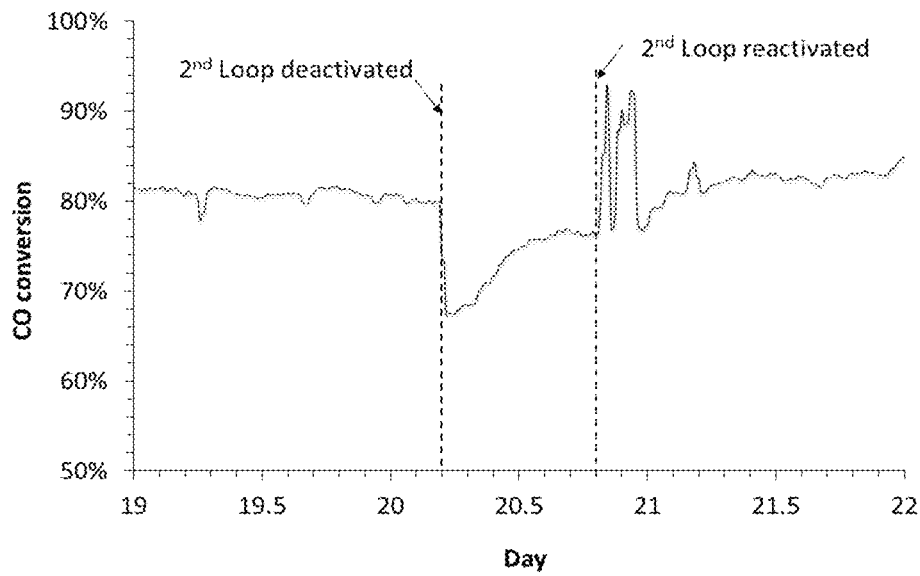
FIG. 5 is a graph displaying the effect of the secondary loop on CO conversion based on experimental results from a 6 meter high reactor.

The effect of the second loop on CO conversion during the same testing period is shown in FIG. 5. An immediate drop in CO conversion was observed after the secondary loop was deactivated, due to the decrease in riser holdup and thus a decrease in mass transfer area. This situation was slowly alleviated by continuously increasing the loop pump, which increased the downcomer holdup. However, this approach was much less effective than the reactivation of the secondary loop on Day 20.8.

Figure 6:
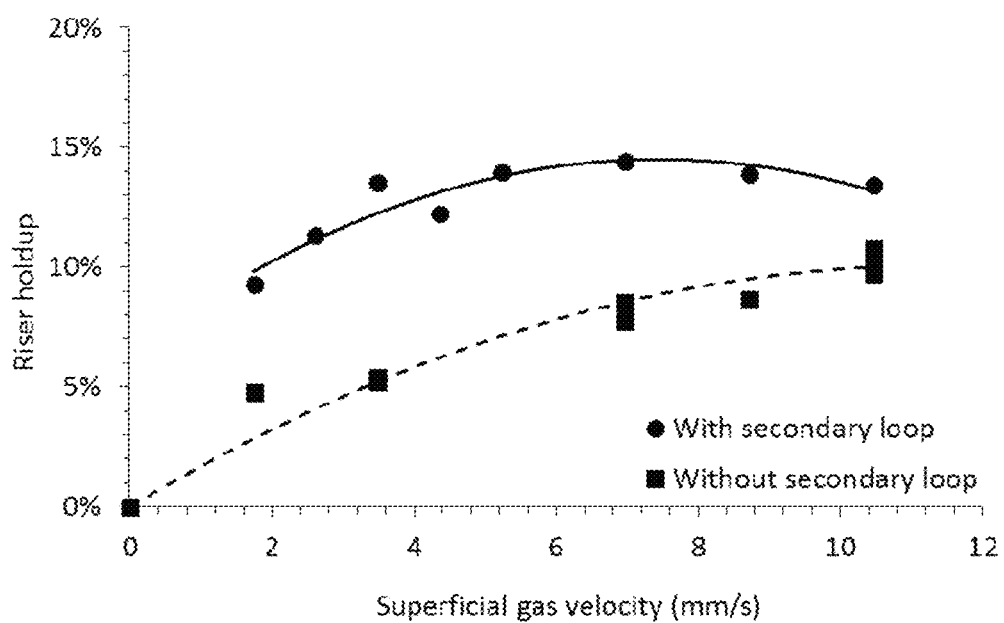
FIG. 6 is a graph displaying the effect of the secondary loop on the riser holdup based on experimental results from a 3 meter high reactor.

The effect of the secondary loop on riser holdup at different inlet gas flow rates was also investigated in a smaller reactor, with a riser diameter of 3 inches and a height of the 1.1 m. The separator of this small reactor had a diameter of 6 inches and an effective height of 270 mm. The diameter of the downcomer was 1.5 inch and the diameter of the secondary loop was 0.5 inch. The results in FIG. 6 show that with the secondary loop, the riser holdup is significantly increased, especially at lower superficial gas flow rates. There appears to be an upper limit of riser holdup at around 15%, which is related to the flow regime changes in such a small reactor. However, the positive holdup effects of the secondary loop persist.

Figure 7:
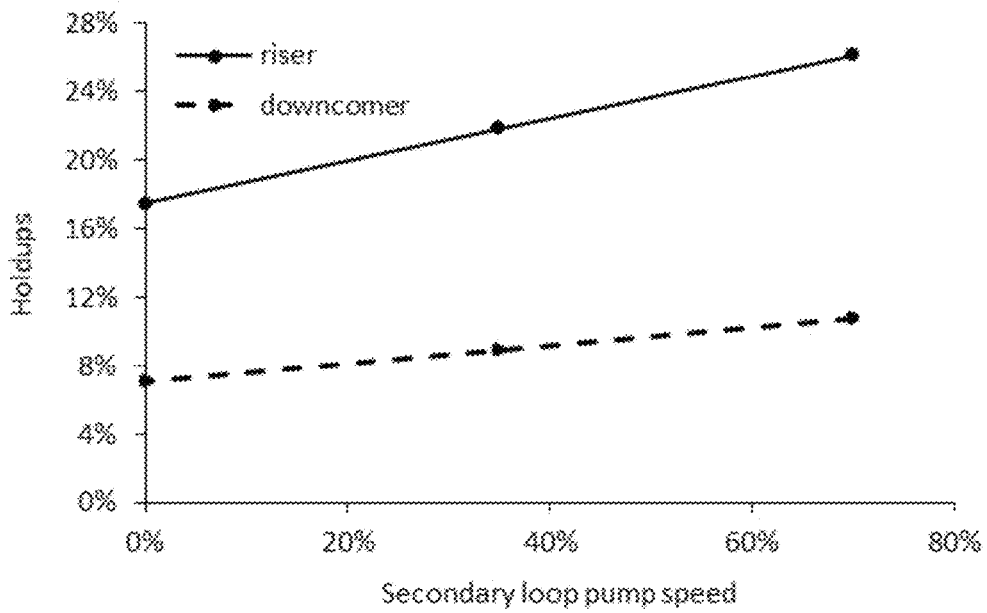
FIG. 7 is a graph displaying the effect of secondary loop pump speed on riser and downcomer holdup based on experimental results from a 10 meter high reactor.
Figure 8:
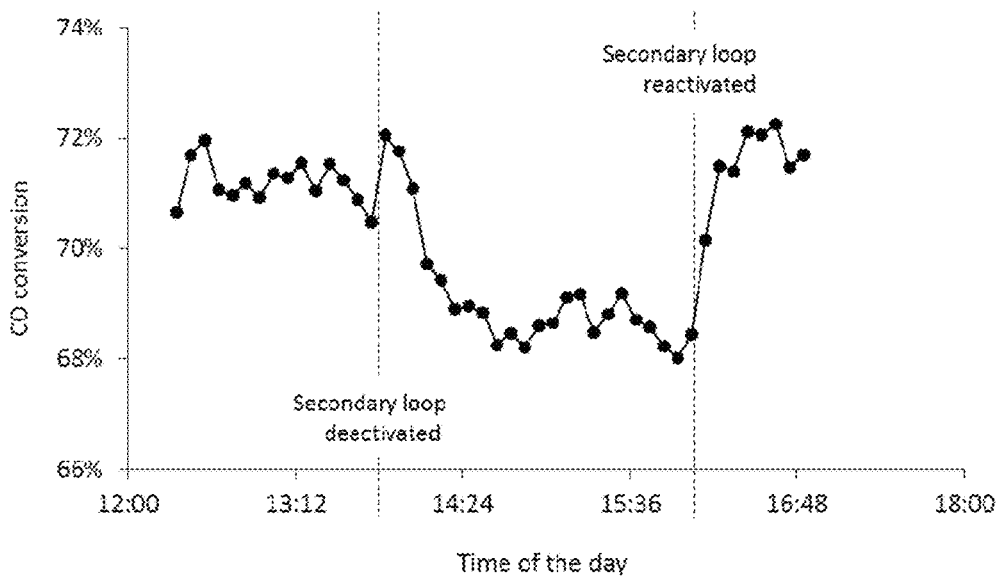
FIG. 8 is a graph displaying the effect of secondary loop pump speed on CO conversion based on experimental results from a 10 meter high reactor.

Experiment 2: Effect of the Secondary Loop on Gas Hold Up and CO Conversion at Larger Scale Similar hydrodynamics experiments investigating the effect of the secondary loop were undertaken in larger 10 meter high reactors, with a 1 meter riser diameter and 0.5 meter downcomer. The diameter of the secondary loop was 2 inch. As shown is FIGS. 7 and 8, the results were similar. It can be seen in FIG. 7 that both the riser and downcomer holdups increased linearly with an increase in secondary loop pump speed, wherein mass transfer should improve accordingly. FIG. 8 shows the effect of the secondary loop on CO conversion from another test in a reactor of the same size.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of O2 that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired products) from particular stages, such as, for example, the bioreactor production stage (e.g. removal of ethanol by distillation).

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method for increasing mass transfer of a gaseous substrate to a fermentation broth in a forced-circulation loop fermentation vessel comprising a riser section wherein a liquid fermentation broth and the gaseous substrate are flowed concurrently upwards and a downcomer section wherein the liquid fermentation broth and the gaseous substrate are flowed concurrently downward, the method comprising:
   (a) providing a gaseous substrate to the fermentation vessel comprising a liquid nutrient medium and one or more microorganism;
   (b) fermenting the gaseous substrate to produce a fermentation broth and at least one product;
   (c) circulating the fermentation broth and the gaseous substrate through the riser section and the downcomer section of the fermentation vessel; and
   (d) removing at least a portion of the fermentation broth containing said nutrient medium, one or more microorganism, and the gaseous substrate from the bottom of the downcomer section and circulating it to the top of the riser section via a secondary loop, wherein the fermentation broth enters the top of the riser section via at least one nozzle thereby increasing mass transfer of the gaseous substrate into the fermentation broth.

2. A method for reducing foam in the headspace of a forced-circulation loop fermentation vessel comprising a riser section wherein a liquid fermentation broth and a gaseous substrate are flowed concurrently upward and a downcomer section wherein the liquid fermentation broth and the gaseous substrate are flowed concurrently downward, the method comprising:
   (a) providing a gaseous substrate to the fermentation vessel comprising a liquid nutrient medium and one or more microorganism;
   (b) fermenting the gaseous substrate to produce a fermentation broth and foam present in the headspace of the fermentation vessel and at least one product;

(c) removing at least a portion of the fermentation broth containing said nutrient medium, one or more microorganism, and the gaseous substrate from the downcomer section of the fermentation vessel; and (d) circulating the at least portion of the fermentation broth from step (c) to the top of the riser section via a secondary loop, wherein the fermentation broth enters the headspace via at least one nozzle;

wherein the fermentation broth entering the headspace reduces foam present within the fermentation vessel.

3. The method of claim 1 wherein the gaseous substrate is selected from the group consisting of CO, $CO_2$, $H_2$ and mixtures thereof.

4. The method of claim 1 wherein the gaseous substrate is provided to the bottom of the riser section of the fermentation vessel.

5. The method of claim 1 wherein the fermentation vessel comprises at least one pumping means to circulate fermentation broth through the riser section and the downcomer section of the fermentation vessel.

6. The method of claim 1 wherein the secondary loop comprises at least one secondary pumping means.

7. The method of claim 1 wherein the secondary loop further comprises a cell recycle module.

8. The method of claim 2 wherein the secondary loop further comprises a cell recycle module.

9. The method of claim 1 wherein the at least one nozzle comprises a showerhead.

10. The method of claim 2 wherein the at least one nozzle comprises a showerhead.

11. The method of claim 1 wherein the one or more microorganism is selected from the group consisting of *Clostridium, Moorella, Oxobacter, Peptostreptococcus, Acetobacterium, Eubacterium*, and *Butyribacterium.*

12. The method of claim 2 wherein the one or more microorganism is selected from the group consisting of *Clostridium, Moorella, Oxobacter, Peptostreptococcus, Acetobacterium, Eubacterium*, and *Butyribacterium.*

13. The method of claim 1 wherein the one or more microorganism is selected from the group comprising *Clostridium autoethanogenum* and *Clostridium ljungdahlii.*

14. The method of claim 1 wherein the at least one product is selected from the group consisting of ethanol, acetic acid and 2,3-butanediol.

15. The method of claim 2 wherein the at least one product is selected from the group consisting of ethanol, acetic acid and 2,3-butanediol.

* * * * *